United States Patent
Böhm-Van Diggelen

(10) Patent No.: US 6,168,434 B1
(45) Date of Patent: Jan. 2, 2001

(54) ORAL HYGIENE APPLIANCE

(76) Inventor: Bernd Böhm-Van Diggelen, Tizianstrasse 33, D-90453 Nürnberg (DE)

(*) Notice: Under 35 U.S.C. 154(b), the term of this patent shall be extended for 0 days.

(21) Appl. No.: 09/341,920

(22) PCT Filed: Jan. 18, 1998

(86) PCT No.: PCT/DE98/00143
§ 371 Date: Jul. 21, 1999
§ 102(e) Date: Jul. 21, 1999

(87) PCT Pub. No.: WO98/31297
PCT Pub. Date: Jul. 23, 1998

(30) Foreign Application Priority Data

Jan. 21, 1997 (DE) .......................................... 297 00 952 U
Oct. 9, 1997 (DE) .......................................... 297 17 964 U

(51) Int. Cl.⁷ .............................. A61C 3/00; A61C 3/06; A61C 15/00; A45D 44/18
(52) U.S. Cl. .......................... 433/141; 433/142; 132/321; 132/308
(58) Field of Search ............................. 433/141; 132/308, 132/309, 310, 311, 321, 322, 329; 15/167.1

(56) References Cited

U.S. PATENT DOCUMENTS

| | | |
|---|---|---|
| 3,939,522 | 2/1976 | Shimizu . |
| 4,083,078 | 4/1978 | Shimizu . |
| 4,149,815 | 4/1979 | Kawam . |
| 4,428,091 | * 1/1984 | Janssen ................................ 15/167.1 |
| 4,559,662 | * 12/1985 | Kunold ............................... 15/104.94 |
| 5,230,118 | * 7/1993 | Chamma ............................. 15/167.1 |
| 5,353,464 | * 10/1994 | Atkins et al. ....................... 15/167.1 |
| 5,944,519 | * 8/1999 | Griffiths .................................. 433/80 |

FOREIGN PATENT DOCUMENTS

| | | |
|---|---|---|
| 80 06 416 | 7/1980 | (DE) . |
| 36 21 815 | 1/1988 | (DE) . |
| 384416 | 4/1908 | (FR) . |
| 1213092 | 3/1960 | (FR) . |
| 96/06547 | 3/1996 | (WO) . |

* cited by examiner

Primary Examiner—John J. Wilson
Assistant Examiner—Robyn Kieu Doan
(74) Attorney, Agent, or Firm—Venable; Gabor J. Kelemen; Leo J. Jennings

(57) ABSTRACT

An oral hygiene appliance has a spring-elastic working piece, comprising a stamped element made from foam, on the head of an handle. The stamped element is made from closed-cell foam, and only the cells located on the stamping face are opened by the stamping process.

16 Claims, 2 Drawing Sheets

ORAL HYGIENE APPLIANCE

BACKGROUND OF THE INVENTION

The invention relates to an oral hygiene appliance having a spring-elastic foam-like working piece on the head of a handle.

To achieve proper oral hygiene, a number of different kinds of devices are known that are used on the teeth and the periodontium (the supporting structure of the teeth). Such devices are intended to reduce the risk of cavities and to prevent the risk of periodontal disease.

The toothbrush is the best known an most often used device in this category. However, devices are also known that, instead of bristles, have spring-elastic materials on the head of a handpiece the avoidance of bristles is intended to prevent the abrasion damage that they cause to the tooth enamel or dentin (German Patent Disclosure DE 36 21 815 A1 and German Utility Model DE 80 06 416 U1).

If working pieces of spring-elastic, absorbent foams, known from the above references, are used, the cleaning action can be achieved by means of a special embodiment of the surface. This kind of embodiment can, if it is soft enough, provide gum massage, but the cleaning effect is inadequate.

The reason for this is that the foam swells like a sponge with liquid, but the pressure exerted in cleaning the teeth expels the liquid again in part. Forces of adhesion and cohesion in the interior of the foam now cause the compressed form of the foam to be maintained until the liquid has slowly evaporated. Yet in the wet, compressed state, the foam loses its elasticity and its ability to adapt in shape, and thus the cleaning action is reduced.

Dirt particles, bacteria and viruses also penetrate into the interior of an absorbent foam and can be removed or killed only with difficulty.

SUMMARY OF THE INVENTION

The object of the invention is to create an oral hygiene appliance in which the above-described problems originating in soft, absorbent sponges, stiff non-woven materials, and the like, do not occur and with which an overall improved cleaning and massaging action is attainable, and that is more universally usable than previously known toothbrushes.

This object is attained, in an oral hygiene appliance of the type defined at the outset, in that the working piece comprises a stamped element produced from closed-cell foam, such as EVA mixed polymer foam, and the cells located on the stamping face are opened by the stamping.

The advantages attained with the invention are in particular that the cleaning of the teeth is done here with the aid of a synthetic, elastic foam whose cells in the interior are closed on all sides. As a result—for example if an EVA mixed polymer foam is used—the absorption of water and saliva into the interior is virtually impossible. Thus dirt particles or bacteria and viruses cannot penetrate into the foam and settle firmly therein, either.

Nor do any additional forces of adhesion and cohesion, which would impair the elasticity of the foam, occur in the interior of the foam.

Because of the cells with a diameter of approximately 0.2 mm to 0.4 mm that are cut open at the stamping face, the toothpaste can be pressed onto the surface of the tooth and shifted along it. As a result of the varying compression, suction forces can also arise, which are desirable for instance for cleaning the pockets of the gums.

Thus in contrast to the known cleaning devices, the cleaning action of the invention is effected primarily not by scouring and abrasive bristles or non-woven fibers but rather primarily by the cleaning action of the toothpaste itself, in conjunction with a suction/pressure method, in which the action of the ingredients, such as fluorides, whiting, foaming agents, and so forth is reinforced.

Besides being used for gentle cleaning of wound areas, for instance after an operation, such a foam also makes it easier to apply medications.

The last part of the object, of making the oral hygiene appliance more universally usable, is attained by another aspect of the invention in which the end of the handle opposite the head has a continuous, conical channel, extending at a right angle to the surface of the handle, with an opening angle of a maximum of 15°. Into this, interdental cleaners, such as bristle brushes, gum massage sticks, gum stimulators, or the like are inserted, using mounts that are congruent with the channel. The conicity leads to adequate adhesion of the inner dental cleaners inserted into the channel. The advantage of this technique is that one of the known individual devices is dispensed with, and it permits a fast and ergonomic change among the various cleaning technique.

According to the another aspect of the invention the end of the handle opposite the head has a mount for dental floss, which may have at least two, and preferably three lateral notches that firmly clamp the dental floss and that are distributed on the periphery of the handle, each with equal spacings from one another.

According to another aspect, the dental floss is placed with one of its ends approximately 10 cm before the aforementioned end in one of the notches, and then inserted through the open conical channel provided for the interdental cleaner, and pulled tight. In this way, the dental floss can be held firmly on one end via the handle and on the other end by using one's hand. In contrast to known dental floss holders, in which both ends of the dental floss are fastened around a device, not only is an individual device dispensed with, but the way in which the floss is manipulated in the mouth is easier and more exact.

In contrast to purely manual manipulation of the dental floss, the advantage is that there is no need to reach with both hands, which furthermore have to hold the floss, into the oral cavity. In the technique described in accordance with another aspect of the invention, the hands do not reach into the oral cavity at all. Guiding a floss is simpler and more exact. A hygienic improvement is furthermore obtained.

Advantageous refinements are provided, by means of the V-like stamping with the rounded tip of the V, so that adaptation of the surface of the foam to the tooth, which is curved in the oral direction, is improved. The zig-zags, spaced apart by the width of one premolar, can also adapt better to the interdental space.

In another aspect, the stamped element extends on both sides of the head of the handle, while as an alternative to this, the stamped element extends on only one side of the head of the handle, while a brush-like working piece is disposed on the other side of the head. This technique is not only more economical and dispenses with the inconvenient changeover among various devices, but also allows simultaneous cleaning of the occlusal surfaces of the teeth in the upper and lower jaws. For reasons of space, the visible length of the bristles is limited to a maximum of 8 mm.

In another aspect, a recess extending all the way through is made in the head of the handle, in order to receive and firmly hold the stamped element and/or the brush-like working piece, while in another aspect, the retention of the foam is further improved by means of a wedge-like protrusion on the inside surface of the recess in the head.

In another aspect, the stamped element can be introduced with compression into the recess and the head of the handle in such a way that it protrudes to the same extent on both sides of the head and remains firmly clamped after the compression is relieved. The advantage of this version is that a more-complicated way of securing the foam to the head is unnecessary, since the resultant pressing action makes it possible to achieve adequate retention of the foam.

This construction furthermore makes it possible to clean with two foam surfaces at a time, specifically on the occlusal tooth surfaces in the upper and lower jaws, and allows a simple change of the foam, or of the brush-like working piece that according to another aspect is assembled integrally with the stamped element and that protrudes to the same extent from both sides of the head, specifically in accordance with one aspect no more than 8 mm each, so as to have enough space in the oral cavity.

Further details of the invention are shown in the drawing in terms of exemplary embodiments and will be described in further detail below.

DETAILED DESCRIPTION OF THE PREFERRED EMBODIMENTS

Figure 1:
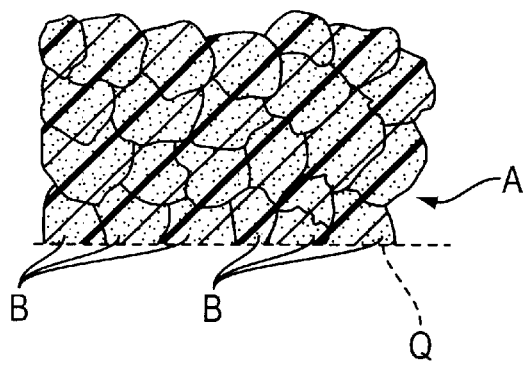
FIG. 1 shows the microstructure of a foam according to the invention.

FIG. 1 shows the closed cells A in the interior of the foam used according to the invention. As a result of a stamping of the material, the cells B are open at the stamping face Q.

Figure 2:
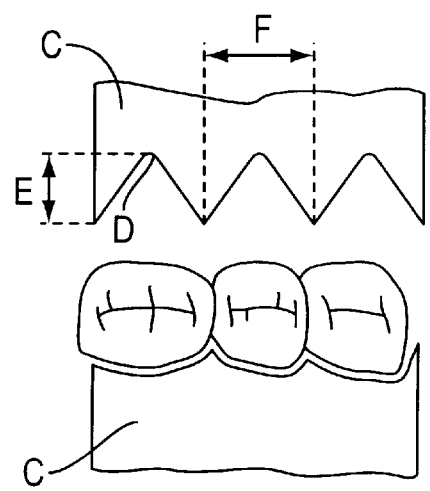
FIG. 2 shows the macroscopic structure of such a foam, stamped out in a zig-zag pattern.

FIG. 2, with a view on the chewing surfaces of three molars, shows two laterally located stamped elements C with a V-10 shaped stamping. The tip of the V D has a radius of curvature of approximately 1 mm and the tips F of the zig-zag profile have a spacing of approximately 7 mm to 10 mm. The depth E of the trough of the zig-zag profile is between 3 mm and 5 mm.

Figure 3:
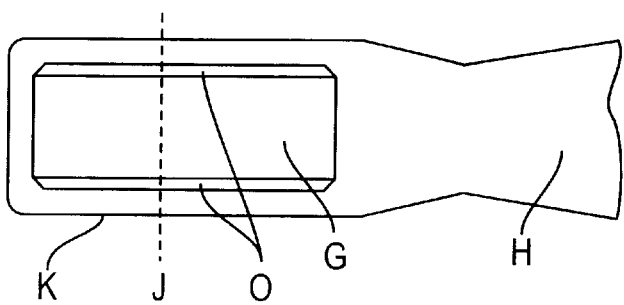
FIG. 3 shows a plan view on a mount for such a foam.

FIG. 3 shows the head K of the handle H with a recess G, into which the stamped element C can be introduced and firmly clamped therein by its own elasticity.

Figure 4:
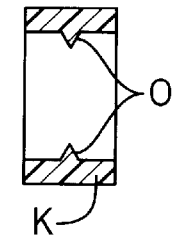
FIG. 4 is a cross section through the mount for the foam taken along the line J in FIG. 3.

FIG. 4 shows the section through the mount along the line J in FIG. 3, with wedge-like protrusions O on the insides of the recess G in the head K. By means of these protrusions O, a better hold of the inserted stamped elements is attained.

Figure 5:
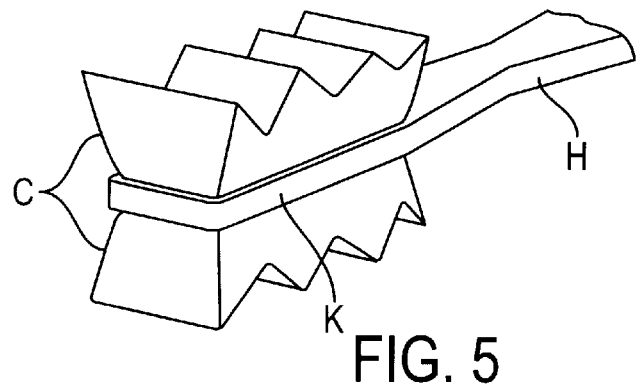
FIG. 5 is an oblique view of a head of an oral hygiene appliance.

FIG. 5 shows the head K of the handle H, with a stamped element C that is inserted into the recess G and is oriented centrally in the recess G.

Figure 6:
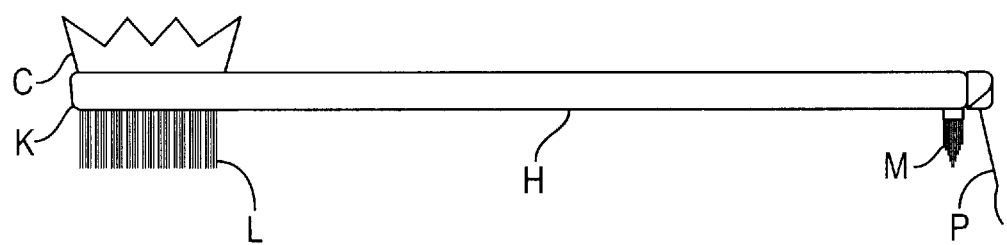
FIG. 6 is a side view of another oral hygiene appliance with a brush element, foam element, and other extras.

FIG. 6 shows the head K with a stamped element C, inserted into the recess G, that extends only on one side of the head K, while on the other side a brush-like working piece L is disposed, which—just like the stamped element C—protrudes by a maximum of 8 mm from the head K.

FIG. 6 also, on the distal end of the handle H opposite the head K, shows an interdental cleaner M, which can be inserted into a continuous conical channel.

Figure 7:
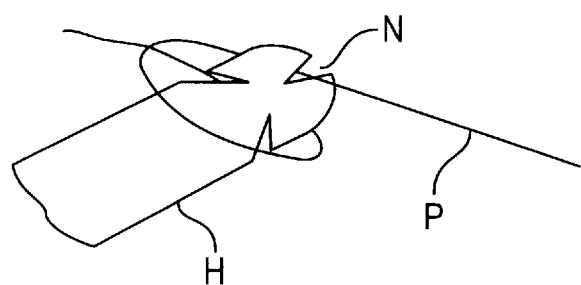
FIG. 7 shows the mounting of dental floss on the handle of the oral hygiene appliance.

FIG. 7 shows the distal end of the handle H, opposite the head, with a mount for securing dental floss P. This mount comprises three laterally rectilinear notches N, which receive the dental floss P; one end of the floss is placed approximately 10 cm before its end in one of the distal notches N, and the short end is wound through the various notches N until it is firmly seated (see also FIG. 6). After that, the end of the floss can also be inserted through the conical channel intended for the interdental cleaner M, which further improves the hold of the dental floss P.

Figure 8:
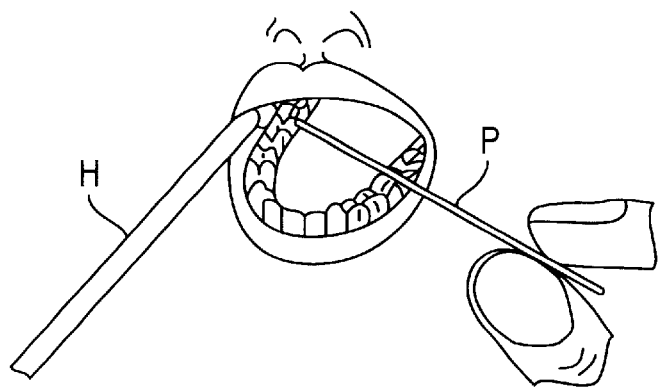
FIG. 8 is a view into the oral cavity, showing the use of dental floss to clean the interstices between teeth.

In this way, the dental floss P can be firmly held on one end via the handle and on the other end by one's hand, as shown in FIG. 8. In contrast to the known dental floss holders, in which both ends of the floss are fastened around some device, not only is an individual device dispensed with but also the way in which the dental floss P is manipulated in the mouth is easier and more exact.

What is claimed is:

1. An oral hygiene appliance having a spring-elastic working piece, comprising a stamped element made with a stamping process from foam and having a stamping face, on the head of a handle,
   wherein the stamped element comprises closed-cell foam, and only the cells located on the stamping face are opened by the stamping process, and the opened cells are adapted to receive cleaning agents and to apply medications.

2. The oral hygiene appliance of claim 1, characterized in that a V-like stamping of a hexahedral foam produces a zigzag profile, seen in the stamping direction, at the stamping face.

3. The oral hygiene appliance of claim 2, characterized in that the crests of the zig-zag profile have a spacing of 7 mm to 10 mm; the depth of the troughs between crests is between 3 mm and 5 mm; and the tip of the V has a radius of curvature of approximately 1 mm.

4. The oral hygiene appliance of claim 1, characterized in that the stamped element extends on both sides of the head of the handle.

5. The oral hygiene appliance of claim 1, characterized in that the stamped element extends on only one side of the head of the handle, while a brush-like working piece is disposed on the other side of the head.

6. The oral hygiene appliance of claim 5, characterized in that the head of the handle has a recess (G) extending all the way through for receiving and firmly holding one of the stamped element and the brushlike working piece.

7. The oral hygiene appliance of claim 6, characterized in that the inside of the recess in the head of the handle has a wedge-like protrusion.

8. The oral hygiene appliance of claim 6, characterized in that the stamped element can be introduced with compression into the recess and the head of the handle in such a way that it protrudes to the same extent on both sides of the head and remains firmly clamped after the compression is relieved.

9. The oral hygiene appliance of claim 6, characterized in that the stamped element and the brush-like working piece are assembled into a one-piece working piece, and the stamped element can be introduced with compression into the recess and the head of the handle in such a way that the one-piece working piece protrudes to the same extent on both sides of the head.

10. The oral hygiene appliance of claim 9, characterized in that the visible length of both the stamped element on one side of the head and of the brush-like working piece on the opposite side of the head does not exceed 8 mm each.

11. An oral hygiene appliance of claim 1,
characterized in that the end of the handle opposite the head has a continuous, conical channel, extending at a right angle to the surface of the handle), with an opening angle of a maximum of 15° for receiving and firmly holding interdental cleaners, such as bristle brushes, gum massage sticks, gum stimulators, or the like.

12. An oral hygiene appliance having a spring-elastic foam-like working piece on the head of a handle, in particular of one of claims 1 through 11, characterized in that the end of the handle opposite the head has a mount for dental floss.

13. The oral hygiene appliance of claim 12, characterized in that the mount comprises at least two and preferably three lateral notches in that firmly clamp the dental floss and that are distributed on the periphery of the handle, each with equal spacings from one another.

14. The oral hygiene appliance of claim 13, characterized in that the dental floss is placed with one of its ends approximately 10 cm before the aforementioned end in one of the notches, and then inserted through the open conical channel provided for the interdental cleaner, and pulled tight.

15. The oral hygiene appliance of claim 1, wherein the closed-cell foam is EVA mixed polymer foam.

16. The oral hygiene appliance of claim 1, wherein the opened cells are adapted to receive toothpaste.

* * * * *